United States Patent
Venturino et al.

(10) Patent No.: US 7,001,167 B2
(45) Date of Patent: Feb. 21, 2006

(54) APPARATUS AND FORM FOR MAKING AN AIR FORMED FIBROUS WEB

(75) Inventors: Michael B. Venturino, Appleton, WI (US); Susan J. Daniels, Neenah, WI (US); Steven P. Milanowski, San Marcos, CA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 128 days.

(21) Appl. No.: 10/207,929

(22) Filed: Jul. 30, 2002

(65) Prior Publication Data

US 2004/0023583 A1 Feb. 5, 2004

(51) Int. Cl.
*B27N 3/08* (2006.01)

(52) U.S. Cl. .................. 425/80.1; 425/470; 264/121; 264/517

(58) Field of Classification Search .............. 425/80.1, 425/81.1, 82.1, 83.1, 470, 471; 264/119, 264/121, 517
See application file for complete search history.

(56) References Cited

U.S. PATENT DOCUMENTS

| | | |
|---|---|---|
| 4,005,957 A | 2/1977 | Savich |
| 4,059,114 A | 11/1977 | Richards |
| 4,666,647 A | 5/1987 | Enloe et al. |
| 4,674,966 A | 6/1987 | Johnson et al. |
| 4,761,258 A | 8/1988 | Enloe |
| 4,927,582 A | 5/1990 | Bryson |
| 4,952,128 A | 8/1990 | Marshall et al. |
| 5,145,351 A | * 9/1992 | Rossi .................. 425/80.1 |
| 5,451,442 A | 9/1995 | Pieniak et al. |
| 5,466,409 A | 11/1995 | Partridge et al. |
| 5,514,324 A | 5/1996 | Bachar |
| 5,665,396 A | 9/1997 | Ulman |
| 5,853,628 A | 12/1998 | Varona |
| 6,098,249 A | 8/2000 | Toney et al. |
| 6,319,455 B1 | 11/2001 | Kauschke et al. |
| 6,330,735 B1 | 12/2001 | Hahn et al. |

FOREIGN PATENT DOCUMENTS

| | | |
|---|---|---|
| EP | 0 383 616 A1 | 8/1990 |
| EP | 0 700 673 A1 | 3/1996 |
| EP | 1 210 925 A2 | 6/2002 |
| WO | WO 01/21122 A1 | 3/2001 |
| WO | WO 02/34188 A1 | 5/2002 |

OTHER PUBLICATIONS

International Search Report for PCT US 03/18330, dated Jan. 19, 2004, 7 pages.

* cited by examiner

*Primary Examiner*—Donald Heckenberg
(74) *Attorney, Agent, or Firm*—Senniger Powers

(57) ABSTRACT

Apparatus for forming an air formed fibrous web has a form member on which fluent fibrous material is deposited in an air formed deposition process. The fibrous web may be used as an absorbent core of an absorbent article. The form member has a forming surface with a pocket for making a thicker portion of the fibrous web such as for a liquid holding formation of the absorbent core. The pocket has a bottom surface which is shaped so that additional material will be deposited in the pocket. A form member and an absorbent core made using the apparatus are also disclosed.

14 Claims, 9 Drawing Sheets

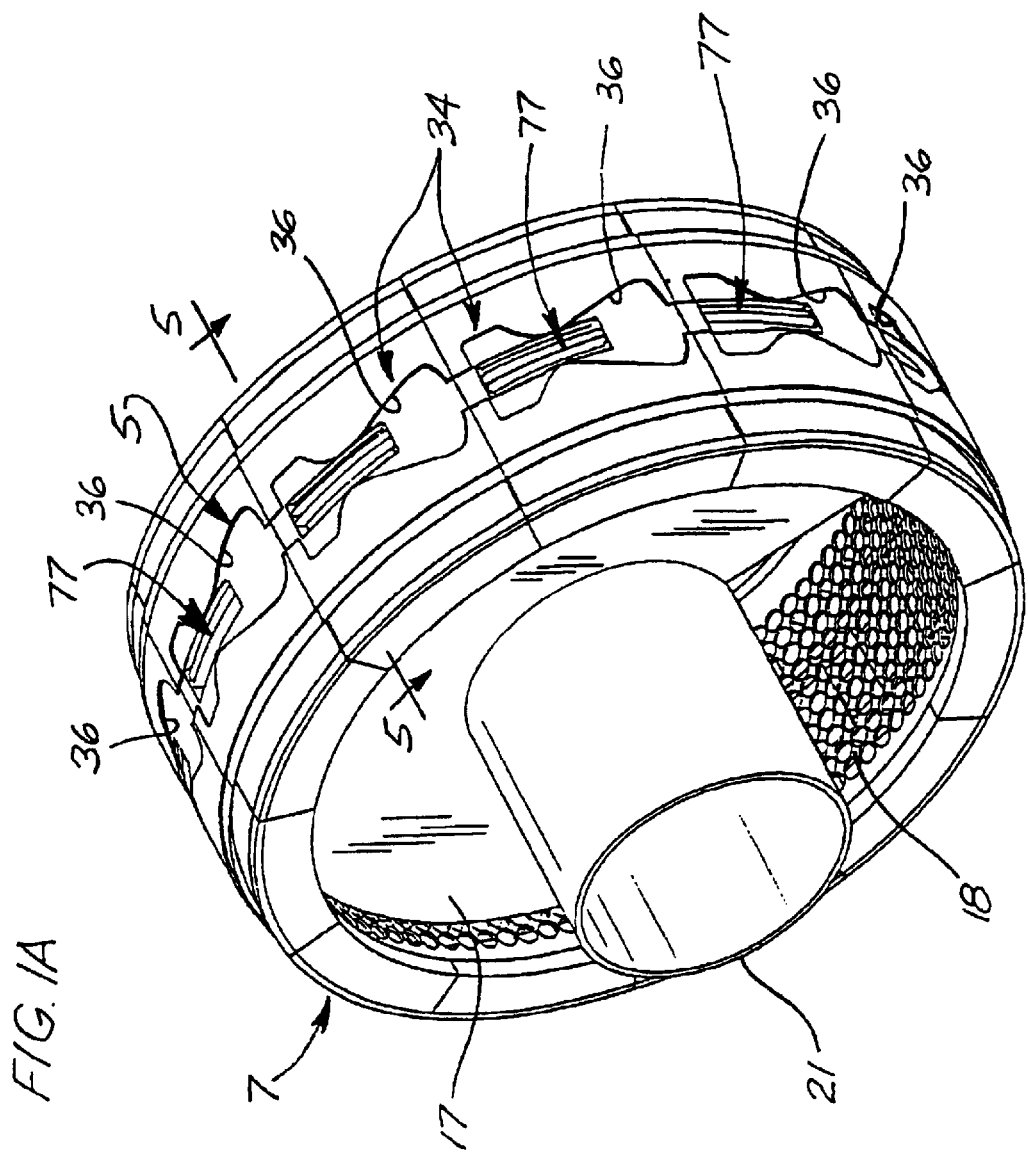

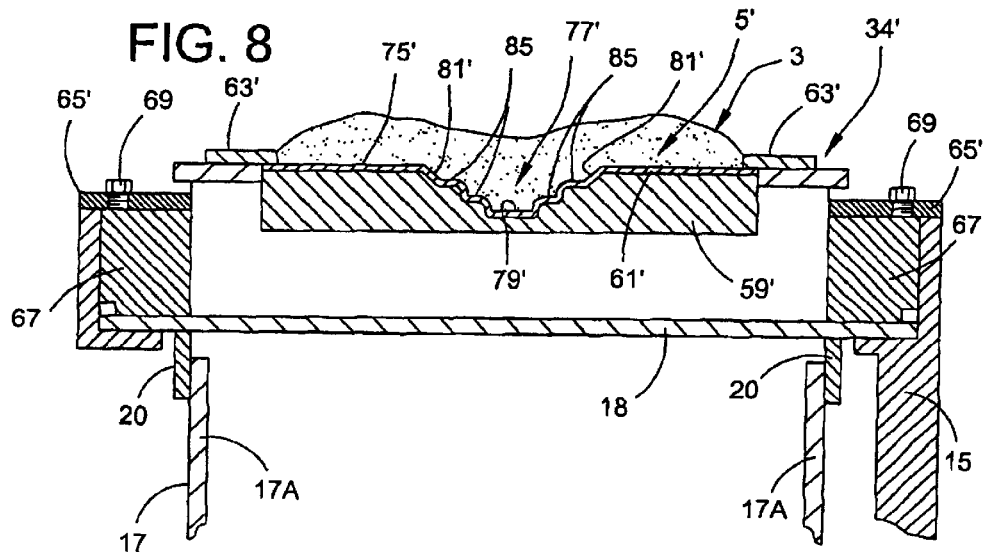
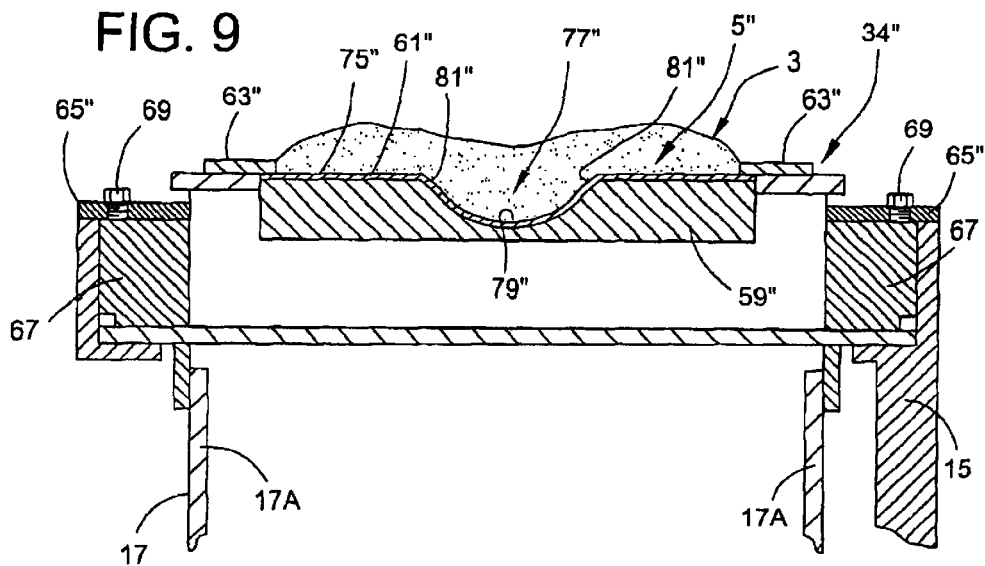

APPARATUS AND FORM FOR MAKING AN AIR FORMED FIBROUS WEB

BACKGROUND OF THE INVENTION

This invention relates generally to apparatus and a form for making an air formed fibrous web and to an absorbent core formed by such a web. The absorbent core can be used for applications such as disposable diapers, child's training pants, feminine care articles, incontinence articles, and the like.

In the general practice of forming fibrous web materials, such as air formed fibrous webs, it has been common to use a fibrous sheet of cellulosic or other suitable absorbent material which has been fiberized in a conventional fiberizer, or other shredding or comminuting device, to form discrete fibers. In addition, particles of superabsorbent material have been mixed with the fibers. The fibers and superabsorbent particles have then been entrained in an air stream and directed to a foraminous forming surface upon which the fibers and superabsorbent particles have been deposited to form an absorbent fibrous web. An absorbent core formed in this fashion has a liquid holding formation which is intended to be the primary repository for liquid to be held by the absorbent core. Thus, the liquid holding formation has conventionally been formed to have a greater amount of fibrous and superabsorbent material (SAM) than surrounding regions and is generally thicker than the surrounding regions of fibrous material.

The forming surfaces used in such systems have been constructed with a perforated plate or wire screen grid and can typically employ a pneumatic flow mechanism, such as vacuum suction apparatus, to produce a pressure differential across the forming surface. The pressure difference causes an airflow through the openings or perforations in the plate or screen of the forming surface. The use of vacuum suction to draw the air-entrained fiber stream onto the forming surface, and pass the airflow through the forming surface is presently employed in high-speed commercial operations. In operation, fibrous material is deposited on the forming surface as it passes through a chamber of the fluent fibers, forming a layer of fibrous material on the forming surface. As the forming layer increases in basis weight (i.e., weight of deposited fiber and SAM per unit area) resistance to air flow through the layer increases. One problem which arises as a result of increased resistance is inadequate deposition of fiber in the area which forms the liquid holding formation. Stated another way, the liquid holding formation may not have a sufficiently higher basis weight than the surrounding regions. The problem can be particularly acute when the area in which material is to be deposited is narrow. There are also problems associated with increased flow resistance such as high weight variability in the absorbent core, fiber damaged caused by excessive retention in the fiberizer, and poor strength caused by insufficient entanglement of fibers in the absorbent core.

The liquid holding formation is typically formed through the provision of a pocket in the forming surface. It has been found that instead of depositing fibrous material to a greater depth in the pocket the depth of material often is nearly the same as in the shallower surrounding regions. Typically, the absorbent core is cut or scarfed after forming on the forming surface so that the surrounding areas end up with a lesser thickness than the region of the liquid holding formation. However, there is often a marked dip in the scarfed surface of the finished absorbent core in the liquid holding formation area indicating that less than a full desired thickness of fibrous material has been deposited. The reduction in the amount of fibrous material (and superabsorbent material) corresponds to a reduction in the quantity of liquid which can be held by the liquid holding formation and the absorbent core. Attempts to remedy this and other problems associated with air flow by control of the vacuum pressure on the forming surface have been complicated and difficult to control.

SUMMARY OF THE INVENTION

Apparatus for use in making a fibrous web has a form or form member with two or more sections. One of the sections has a bottom surface which is spaced different distances from the other section so that more fibrous material will be deposited in the one section than in the other for forming a thicker liquid holding formation.

In one aspect of the present invention, a form for use in making an air formed fibrous web comprises a foraminous surface having a length and a width and adapted to collect fluent fibrous material driven by fluid pressure toward the foraminous surface to form the fibrous web. The foraminous surface includes a first section for collecting fluent fibrous material to a first depth and a second section for collecting fluent fibrous material to a second depth greater than the first depth. A third section connects the first and second sections. The second section includes a bottom surface spaced below the first section different distances over the bottom surface.

In another aspect of the present invention, apparatus for forming a fibrous web comprises a form and a delivery chute adapted to deliver fluent fibrous material generally to the form. A vacuum source can apply a vacuum to draw the fluent material onto the form. The form comprises a foraminous surface having a length and a width and adapted to collect fluent fibrous material driven by fluid pressure toward the foraminous surface to form the fibrous web. The foraminous surface includes a first section for collecting fluent fibrous material to a first depth and a second section for collecting fluent fibrous material to a second depth greater than the first depth. A third section connects the first and second sections. The second section includes a bottom surface which is spaced below the first section different distances over the bottom surface.

In still another aspect of the present invention, an absorbent core of air formed fibrous material has a liquid holding formation with a peripheral edge. The liquid holding formation is elongate and has a surface formed with channels extending generally lengthwise of the core for use in distributing liquid lengthwise of the core and impeding flow of liquid transversely of the core. The ends of the channels terminate a distance spaced from the peripheral edge of the liquid holding formation to impede flow of liquid in the channels past the peripheral edge of the liquid holding formation.

BRIEF DESCRIPTION OF THE DRAWINGS

FIG. 1A is a schematic perspective of a drum of the apparatus;

FIG. 8 is a fragmentary section similar to FIG. 5, but showing the second, modified form member of FIG. 7;

FIG. 9 is a fragmentary section similar to FIG. 5, but showing a third, modified form member;

Corresponding reference characters indicated corresponding parts throughout the several views of the drawings.

DETAILED DESCRIPTION OF THE DRAWINGS

Figure 1:
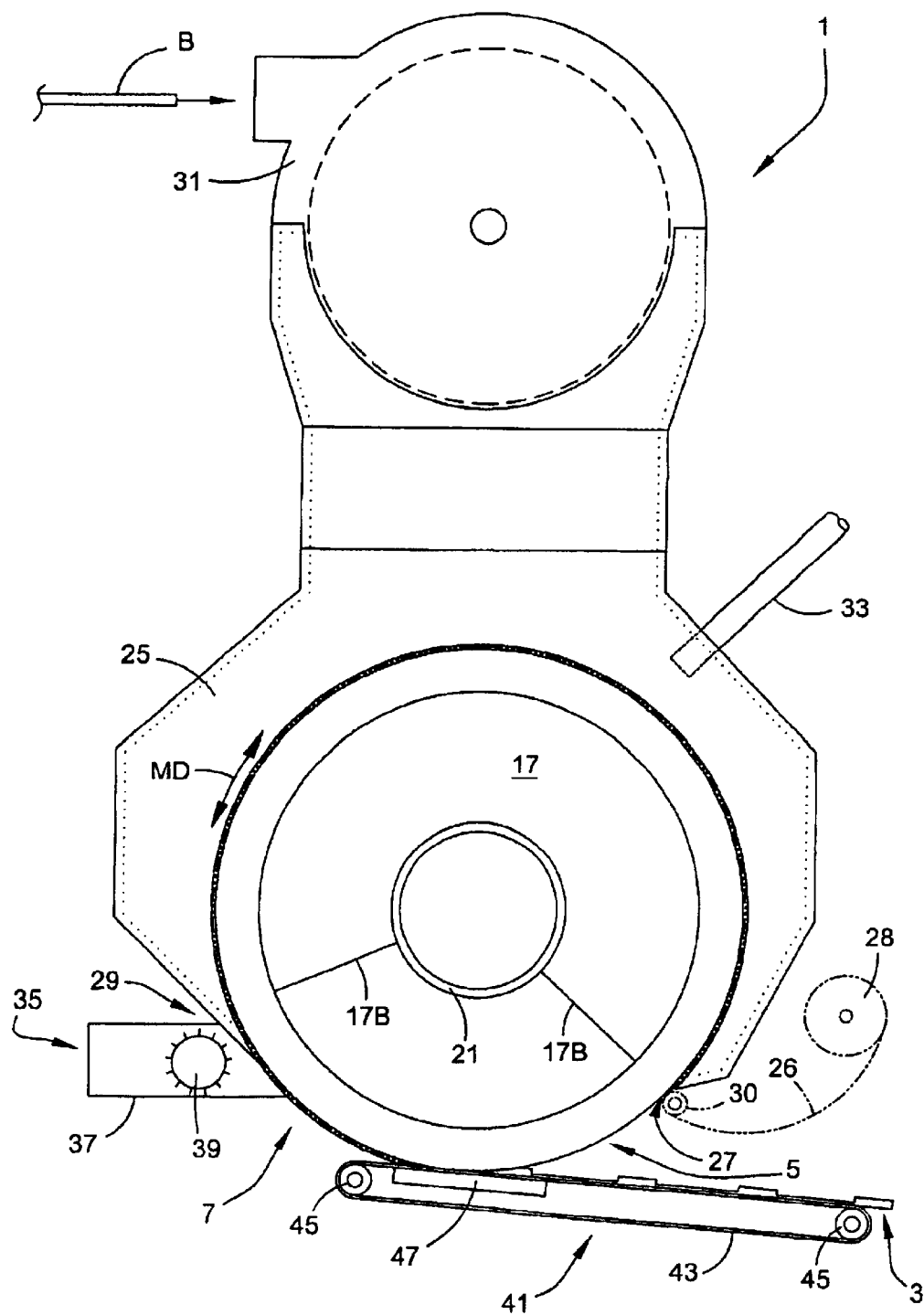
FIG. 1 is a schematic, side elevation of apparatus for forming an air formed fibrous web.
Figure 2:
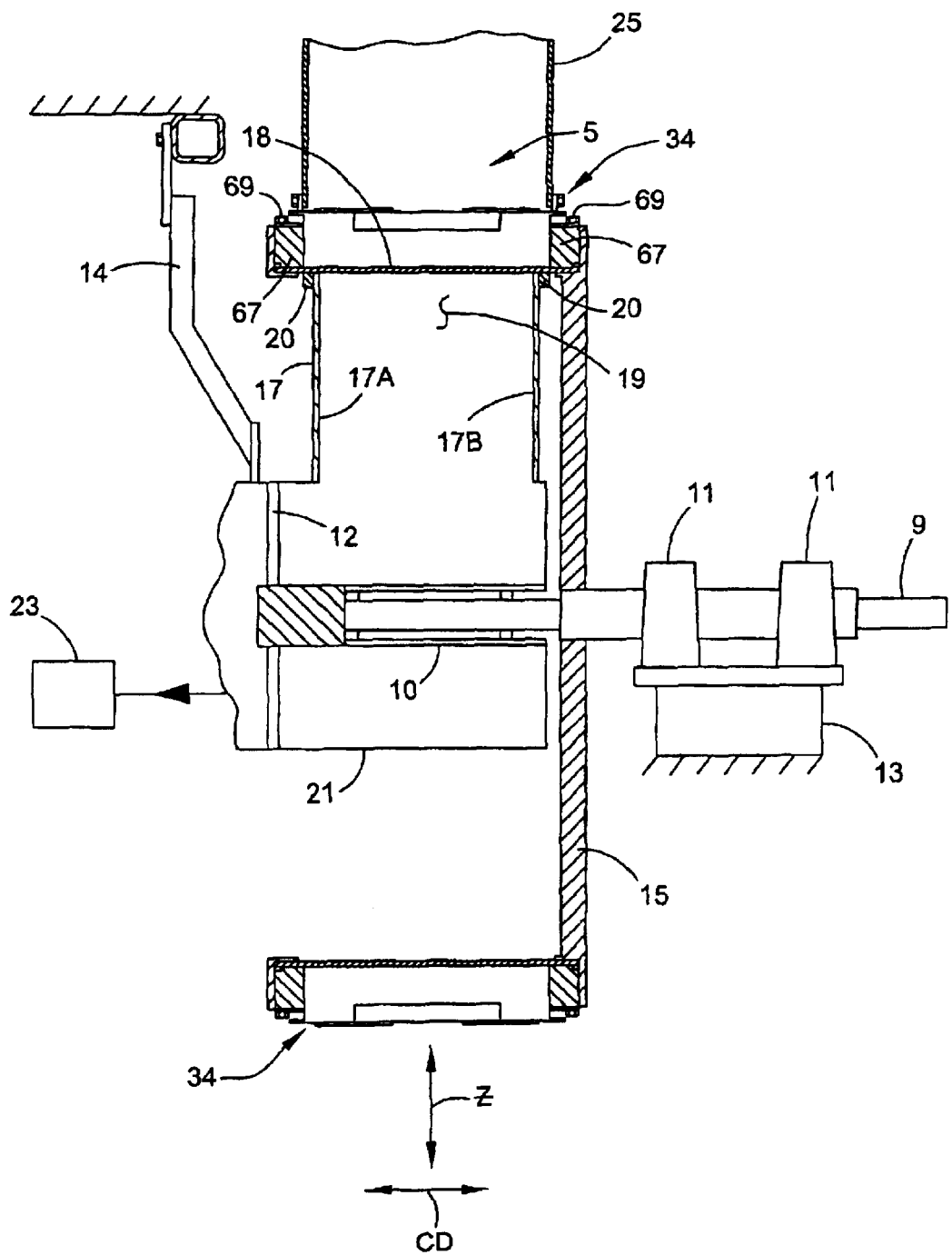
FIG. 2 is a fragmentary cross-section the apparatus of FIG. 1.

Referring to FIGS. 1, 1A and 2, for purposes of the present description the apparatus has a machine-direction MD which extends generally in the direction of motion of the machine, a lateral cross-direction CD which extends transversely to the machine direction, and a z-direction Z. For the purposes of the present disclosure, the machine-direction MD is the direction along which a particular component or material is transported lengthwise along and through a particular, local position of the apparatus. The cross-direction CD lies generally within the plane of the material being transported through the process, and is transverse to the local machine-direction MD. The z-direction Z is aligned substantially perpendicular to both the machine-direction MD and the cross-direction CD, and extends generally along a depthwise, thickness dimension of the material.

Apparatus 1 constructed according to the principles of the present invention for forming a fibrous web 3 can include a movable, foraminous forming surface 5 extending around the circumference of a drum 7 (the reference numerals designating their subjects generally). The drum 7 is mounted on a shaft 9 connected by bearings 11 to a support 13. As shown in FIG. 2, the drum includes a circular wall 15 connected to the shaft 9 for conjoint rotation therewith. The shaft 9 is driven in rotation by a suitable motor or line shaft (not shown) in a counterclockwise direction as seen in FIG. 1. The wall 15 cantilevers the forming surface 5 and the opposite side of the drum 7 is open. A vacuum duct 17 located radially inwardly of the forming surface extends over an arc of the drum interior. The vacuum duct 17 has an arcuate, elongate entrance opening 19 under the foraminous forming surface 5, as will be described in more detail hereinafter, for fluid communication between the vacuum duct and the forming surface. The vacuum duct 17 is mounted on and in fluid communication with a vacuum conduit 21 connected to a vacuum source 23 (represented diagrammatically in FIG. 2). The vacuum source 23 may be, for example, an exhaust fan. The vacuum duct 17 is connected to the vacuum supply conduit 21 along an outer peripheral surface of the conduit, and extends circumferentially of the conduit. The vacuum duct 17 projects radially outwardly from the vacuum conduit 21 toward the forming surface 5 and includes axially spaced side walls 17A and angularly spaced end walls 17B. The shaft 9 extends through the wall 15 and into the vacuum supply conduit 21 where it is received in a bearing 10 connected to a brace 12 within the conduit. The bearing 10 is sealed with the vacuum supply conduit 21 so that air is not drawn in around the shaft 9 where it enters the conduit. The brace 12 and entire conduit 21 are supported by an overhead mount 14.

A drum rim 18 is mounted on the wall 15 of the drum 7 and has a multiplicity of holes over its surface area to provide a substantially free movement of air through the thickness of the rim. The rim 18 is generally tubular in shape and extends around the axis of rotation of the shaft 9 near the periphery of the wall 15. The rim 18 is cantilevered away from the drum wall 15, and has a radially inward-facing surface positioned closely adjacent to the entrance opening 19 of the vacuum duct 17. To provide an air resistant seal between the rim 18 and the entrance opening 19 of the vacuum duct 17, rim seals 20 are mounted on the inward-facing surface of the rim 18 for sliding sealing engagement with the walls 17A of the vacuum duct. Seals (not shown) are also mounted on the end walls 17B of the vacuum duct 17 for sliding sealing engagement with the inward-facing surface of the rim 18. The seals may be formed of a suitable material such as felt to permit the sliding sealing engagements.

The apparatus 1 further includes a forming chamber 25 through which the forming surface 5 is movable. The forming chamber 25 has an entrance 27 where the forming surface 5 enters the chamber substantially free of fibrous material, and an exit 29 where the forming surface leaves the chamber substantially filled with fibrous material. A fiberizer 31 provides fibrous material into the forming chamber 25, and the vacuum source 23 (FIG. 2) creates a vacuum pressure in the vacuum duct 17 relative to the interior of the chamber 25. As the forming surface 5 enters and then traverses through the forming chamber 25, the component materials of the fibrous web 3 are operatively carried or transported by an entraining air stream that is drawn through the forming surface 5. The pressure differential across the forming surface 5 causes the fluent fibers in the chamber 25 to be drawn to the forming surface.

The selected fibrous material may be suitably derived from a batt B of cellulosic fibers (e.g., wood pulp fibers) or other source of natural and/or synthetic fibers, which has been disintegrated, in a manner well known in the art, to provide an operative quantity of individual, loose fibers. The fiberizer 31 receives a selected web-forming material, converts the web-forming material into individual fibers, and delivers the fibers into the forming chamber 25. In the illustrated configuration, the fiberizer 31 can be a rotary hammer mill or a rotatable picker roll. However, it is to be understood that fibers may be provided in other ways by other devices within the scope of the present invention. Suitable fiberizers are available from Paper Converting Machine Company, a business having offices located in Green Bay, Wis., U.S.A.

Other component materials for producing the fibrous web 3 may also be delivered into the forming chamber 25. For example, particles or fibers of superabsorbent material may be introduced into the forming chamber 25 by employing conventional mechanisms, such as pipes, channels, spreaders, nozzles and the like, as well as combinations thereof. In the illustrated embodiment, the superabsorbent material is delivered into the forming chamber 25 by employing a schematically represented delivery conduit and nozzle system 33. The fibers, particles and other desired web material may be entrained in any suitable gaseous medium. Accordingly, any references herein to air as being the entraining medium should be understood to be a general reference which encompasses any other operative entraining gas. Superabsorbent materials are well known in the art, and are readily available from various suppliers. For example, FAVOR SMX 880 superabsorbent is available from Stockhausen, Inc., a business having offices located in Greensboro, N.C., U.S.A.; and Drytech 2035 is available from Dow Chemical Company, a business having offices located in Midland, Mich., U.S.A.

The stream of fluent fibers and particles pass through the forming chamber 25 for deposition onto the forming surface 5. The forming chamber 25 can serve to direct and concentrate the air-entrained fibers and particles, and to provide a desired velocity profile in the air-entrained stream of fibers and particles. Typically, the forming chamber 25 is supported by suitable structural members, which together form a support frame for the forming chamber. The frame may be anchored and/or joined to other suitable structural components, as necessary or desirable. The construction and operation of such forming chambers 25 is well known and will not be described in further detail herein. Instead of applying the fibers (and SAM) directly to the forming surface, it is known to place a porous substrate over the forming surface on which the fibers are deposited. Suitable substrates may, for example, be formed from tissue, spunbond, nonwoven or woven materials. A web 26 of substrate is shown in phantom in FIG. 1 to extend from a roll 28 into the entrance 27 of the forming chamber 25. The roll 28 can be held and the web 26 fed out by suitable delivery device (not shown in its entirety) as is known in the art. A roller 30 of the delivery device is shown for guiding the web 26 into the entrance 27. The web 26, when used, overlies the forming surface 5 so that fibers and superabsorbent material are deposited on the web rather than directly on the forming surface 5. The vacuum causes the web 26 to conform to the shape of the forming surface 5. The use of such substrates desirably reduces the amount of fiber which passes completely through the forming surface 5 because individual pores of the substrate are smaller than the openings in the forming surface. However for simplicity, the illustrated embodiment will be described hereinafter without reference to the substrate web 26.

The forming surface 5 is illustrated as being part of the forming drum 7, but it is to be understood that other techniques for providing the forming surface 5 may also be employed without departing from the scope of the present invention. For example, the forming surface 5 may be provided by an endless forming belt (not shown). A forming belt of this type is shown in U.S. Pat. No. 5,466,409, entitled FORMING BELT FOR THREE-DIMENSIONAL FORMING APPLICATIONS by M. Partridge et al. which issued on Nov. 14, 1995.

Figure 6:
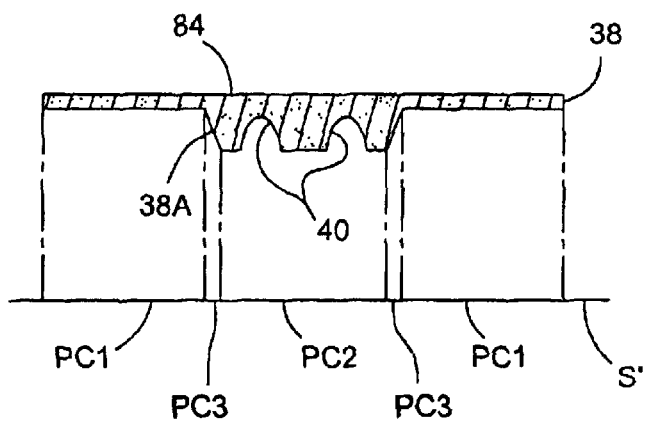
FIG. 6 is a cross section of a scarfed absorbent core formed by apparatus of the present invention.

The foraminous forming surface 5 is defined in the illustrated embodiment by a series of form members 34 which are arranged end-to-end around the periphery of the forming drum 7 and independently attached to the drum. As may be seen in FIG. 1A, the form members 34 each define a substantially identical pattern 36 in which fibrous material is deposited. The patterns 36 correspond to a desired shape of individual absorbent cores 38 (one of which is shown in FIG. 6) which repeats over the circumference of the drum. However, partially repeating or non-repeating pattern shapes may be used with the present invention. Under the influence of the vacuum source 23, a conveying air stream is drawn through the foraminous forming surface 5 into the vacuum duct 17 on the interior of the forming drum 7, and is subsequently passed out of the drum through the vacuum supply conduit 21. As the fluent fibers and particles impinge the foraminous forming surface 5, the air component is passed through the forming surface and the fibers-particles component is retained by the forming surface to form a nonwoven fibrous web 3 thereon. Subsequently, with the rotation of the drum 7, the formed web 3 is removed from the forming surface 5.

The drum 7 carrying the air formed fibrous web 3 deposited on the forming surface 5 in the forming chamber 25 passes out of the chamber through the exit 29 to a scarfing system, generally indicated at 35 in FIG. 1, where excess thickness of the fibrous web can be trimmed and removed to a predetermined extent. The scarfing system includes a scarfing chamber 37 and a scarfing roll 39 which is positioned within the scarfing chamber. The scarfing roll 39 abrades excess fibrous material from the fibrous web 3, and the removed fibers are transported away from the scarfing chamber 37 with a suitable discharge conduit (not shown), as well known in the art. The removed fibrous material may, for example, be recycled back into the forming chamber 25 or the fiberizer 31, as desired. Additionally, the scarfing roll 39 can rearrange and redistribute the web material along the longitudinal machine-direction MD of the web 3 and/or along the lateral cross-direction CD of the web. The profile of the web made by a scarfing roll may be flat (as with scarfing roll 39), but also may be shaped or irregular as desired by selection and arrangement of teeth (not shown) on the scarfing roll.

The rotatable scarfing roll 39 is operatively connected and joined to a suitable shaft member, and is driven by a suitable drive system (not shown). The drive system may include any conventional apparatus, such as provided by a dedicated motor, or a coupling, gear or other transmission mechanism operatively connected to the motor or other drive mechanism employed to rotate the forming drum 7. The scarfing roll system 35 can provide a conventional trimming mechanism for removing or redistributing any excess, z-directional thickness of the air formed fibrous web that has been deposited on the forming surface 5. The scarfing operation can yield a fibrous web having a selected contour on a major face-surface of the fibrous web that has been contacted by the scarfing roll 39. The surface of the scarfing roll can be adjusted to provide a desired contour along the scarfed surface of the fibrous web 3. In the illustrated embodiment, the scarfing roll 39 can, for example, be configured to provide a substantially flat surface along the scarfed surface of the fibrous web 3. The scarfing roll 39 can optionally be configured to provide a non-flat surface. The scarfing roll 39 is disposed in spaced adjacent relationship to the forming surface 5, and the forming surface is translated past the scarfing roll by rotation of the drum 7.

In the illustrated embodiment, the scarfing roll 39 rotates in a direction which moves a contacting surface of the scarfing roll in a counter-direction that is opposite the rotation of the drum 7 and the movement direction of the air formed fibrous web 3. Alternatively, the scarfing roll 39 may be rotated so that the roll surface moves in the same direction as the forming surface 5 on the forming drum 7. In either situation, the rotational speed of the scarfing roll 39 should be suitably selected to provide an effective scarfing action against the contacted surface of the formed fibrous web 3. In like manner, any other suitable trimming mechanism may be employed in place of the scarfing roll 39 assembly to provide a cutting or abrading action to the air formed fibrous web by a relative movement between the fibrous web 3 and the selected trimming mechanism.

After the scarfing operation, the portion of the forming surface 5 that is carrying the air formed fibrous web 3 can be moved to a release zone of the apparatus 1. In the release zone vacuum causes the web 3 to transfer from the forming surface 5 onto a conveyor indicated generally at 41. The release can be assisted by the application of air pressure from the interior of the drum 7. The conveyor 41 receives the formed fibrous web 3 from the forming drum 7, and conveys the web to a collection area or to a location for further processing (not shown). Suitable conveyors can, for example, include conveyer belts, vacuum drums, transport rollers, electromagnetic suspension conveyors, fluid suspension conveyors or the like, as well as combinations thereof. In the illustrated embodiment, the conveyor 41 includes an endless conveyor belt 43 disposed about rollers 45. A vacuum suction box 47 is located below the conveyor belt 43 to remove the web 3 from the forming surface 5. The belt 43 is perforate and the vacuum box 47 defines a plenum beneath the portion of the belt in close proximity to the forming surface so that a vacuum is communicated to the fibrous web 3 on the drum 7. Removal of the web 3 can alternatively be accomplished by the weight of the web, by centrifugal force, by mechanical ejection, by positive air pressure or by some combination or by another suitable method. The positive air pressure can be produced, for example, by a source of compressed air (not shown) such as a fan which generates a pressurized air flow that exerts a force directed outwardly through the forming surface 5. The removed fibrous web includes an interconnected series of absorbent cores, and each body has a selected surface contour which substantially matches the contour provided by the corresponding portions of the forming surface 5 upon which each individual pad was formed. It is also possible to contour the scarfed side of the web 3.

Suitable forming drum systems for producing air formed fibrous webs are well known in the art. For example, see U.S. Pat. No. 4,666,647 entitled APPARATUS AND METHOD FOR FORMING A LAID FIBROUS WEB by K. Enloe et al. which issued May 19, 1987; and U.S. Pat. No. 4,761,258 entitled CONTROLLED FORMATION OF LIGHT AND HEAVY FLUFF ZONES by K. Enloe which issued Aug. 2, 1988; the entire disclosures of which are incorporated herein by reference in a manner that is consistent herewith. Other forming drum systems are described in U.S. Pat. No. 6,330,735, entitled APPARATUS AND PROCESS FOR FORMING A LAID FIBROUS WEB WITH ENHANCED BASIS WEIGHT CAPABILITY by J. T. Hahn et al. which issued Dec. 18, 2001, and U.S. patent application Ser. No. 09/947,128, entitled MULTI-STAGE FORMING DRUM COMMUTATOR by D. P. Murphy et al., filed Sep. 4, 2001, the entire disclosures of which is incorporated herein by reference in a manner that is consistent herewith. Examples of techniques which can introduce a selected quantity of superabsorbent particles into a forming chamber are described in U.S. Pat. No. 4,927,582 entitled METHOD AND APPARATUS FOR CREATING A GRADUATED DISTRIBUTION OF GRANULE MATERIALS IN A FIBER MAT by R. E. Bryson which issued May 22, 1990; the entire disclosure of which is incorporated herein by reference in a manner that is consistent herewith. It will be appreciated that the description of the drum 7 shown in the drawings is exemplary, as other configurations (including those not having a drum for carrying the foraminous forming surface 5) may be employed to produce the fibrous web 3.

Figure 3:
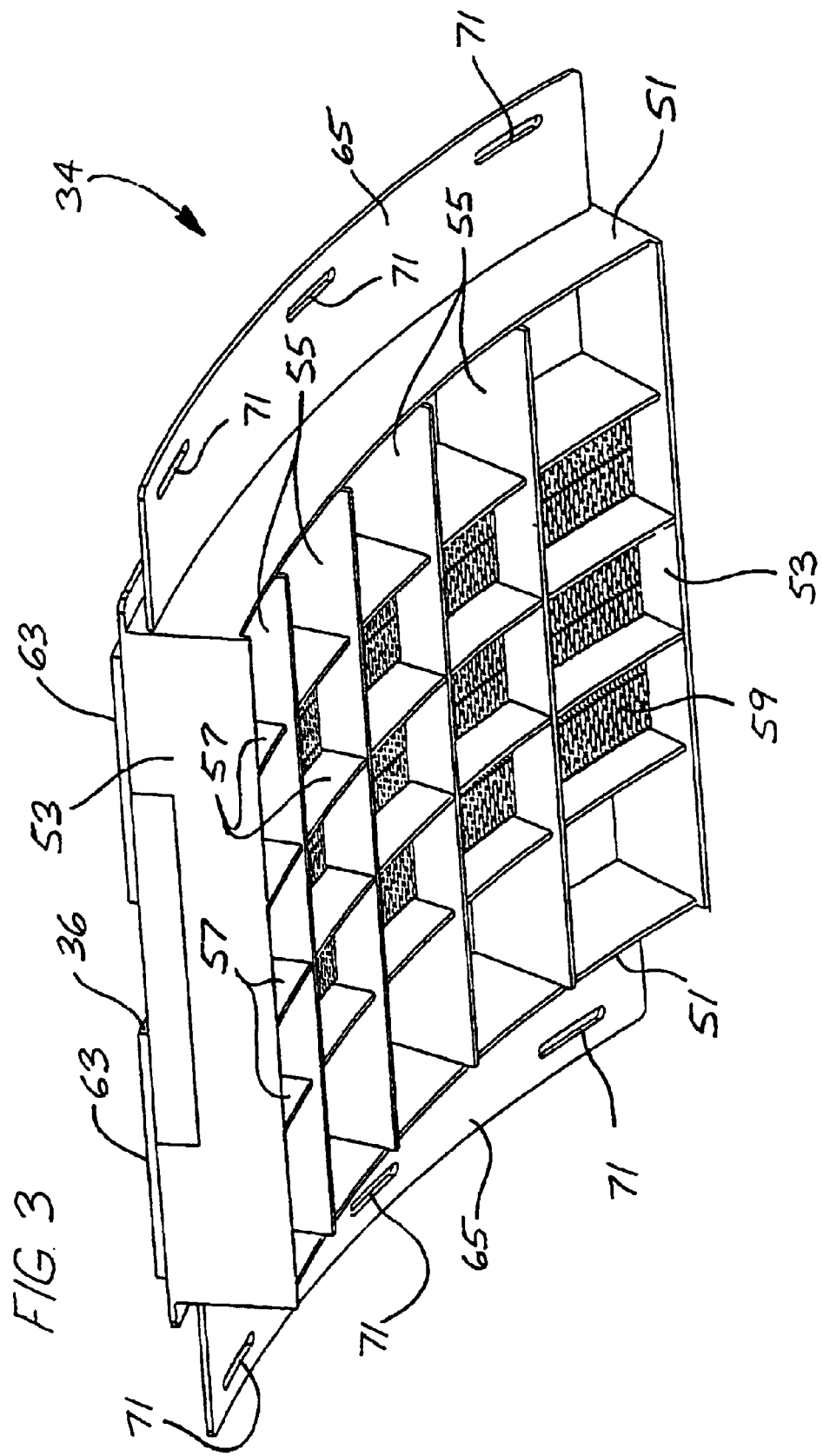
FIG. 3 is a bottom perspective of a form member of the apparatus.

Referring now to FIG. 3, a single form member 34 is shown as removed from the drum 7. As used herein, the term "form" can refer to a single form member 34 or to a collection of form members, such as the form members which extend around the complete circumference of the drum 7. Moreover, it is envisioned that a single form member (not shown) extending around the entire circumference of the drum 7 could be employed. The illustrated form member 34 comprises outer side walls 51 connected to end walls 53 to form a rectangular frame. The side walls 51 are curved along their length to match the arc of the drum 7 over which the individual form members 34 will extend.

Transverse walls 55 extend between the side walls 51 and longitudinal walls 57 extend between the end walls 53 inside the frame. The frame supports the forming surface 5 which in the illustrated embodiment comprises a honeycombed support 59 and a thin, perforated plate 61 (see FIG. 5). The support 59 and perforated plate 61 have the same upper surface shape. The support 59 underlies and provides strength for the perforated plate 61 to hold it in a fixed configuration under the load applied by the vacuum. The support 59 permits air to pass freely through it by virtue of the relative larger openings of its honeycomb structure. The openings can have any desired cross-sectional shape, such as circular, oval, hexagonal, pentagonal, other polygonal shape or the like, as well as combinations thereof, and need not be in a honeycomb arrangement. Such support structures are well known in the art, and can be composed of various materials, such as plastic, metal, ceramics and the like, as well as combinations thereof. The smaller holes in the perforated plate 61 also allow passage of air, but are sized to capture the fibrous material and prevent its passage through the forming surface 5. The perforate plate 61 may be replaced by a screen, a wire mesh, a hard-wire cloth or the like, as well as combinations thereof. It is envisioned that if a sufficiently rigid, self-supporting material could be found for the perforate plate 61, the support 59 could be omitted.

Masking plates 63 are attached to the radially outwardly facing surface of the form member 34 to mask portions of the perforated plate 61 and support 59 to prevent air from passing through the masked portions and hence prevent deposition of fibrous material. The patterns 36 are defined by the shape of the masking plates 63. The form member 34 is mounted on the drum 7 by a pair of wings 65 attached to and extending laterally outwardly from respective side walls 51. When applied to the drum 7 as shown in FIG. 2, the wings 65 of the form member 34 overlie respective, axially spaced mounting rings 67 mounted on the rim 18 at its opposite lateral edges. The form member 34 is releasably secured to the mounting rings 67 by bolts 69 passing through elongate openings 71 in the wings and threadably received in holes (not shown) formed in the rings. The elongation of the openings 71 allows some variation in the circumferential position of the form member 34, facilitating placement of the forming members on the drum 7.

Figure 4:
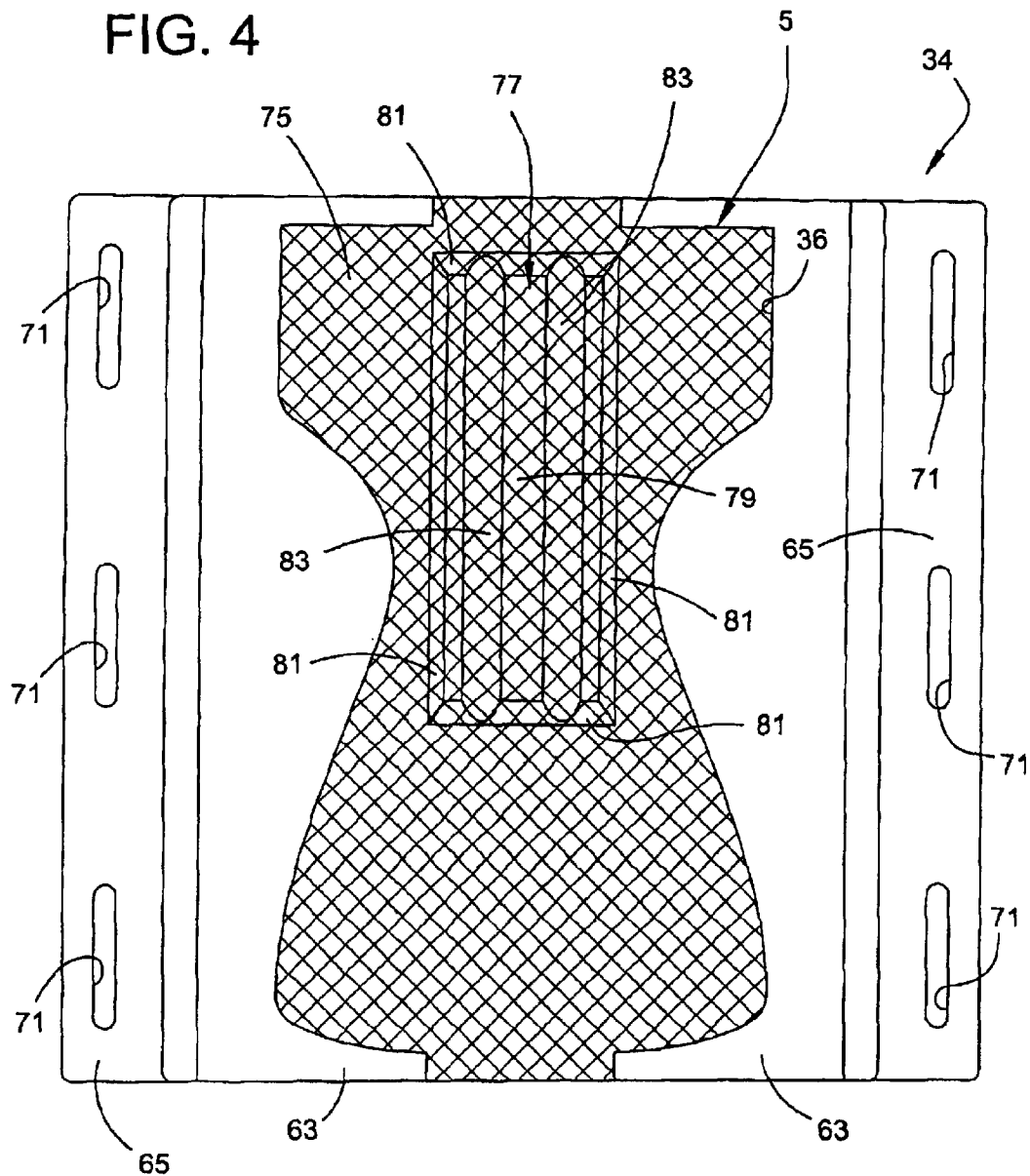
FIG. 4 is a top plan view of the form member.
Figure 5:
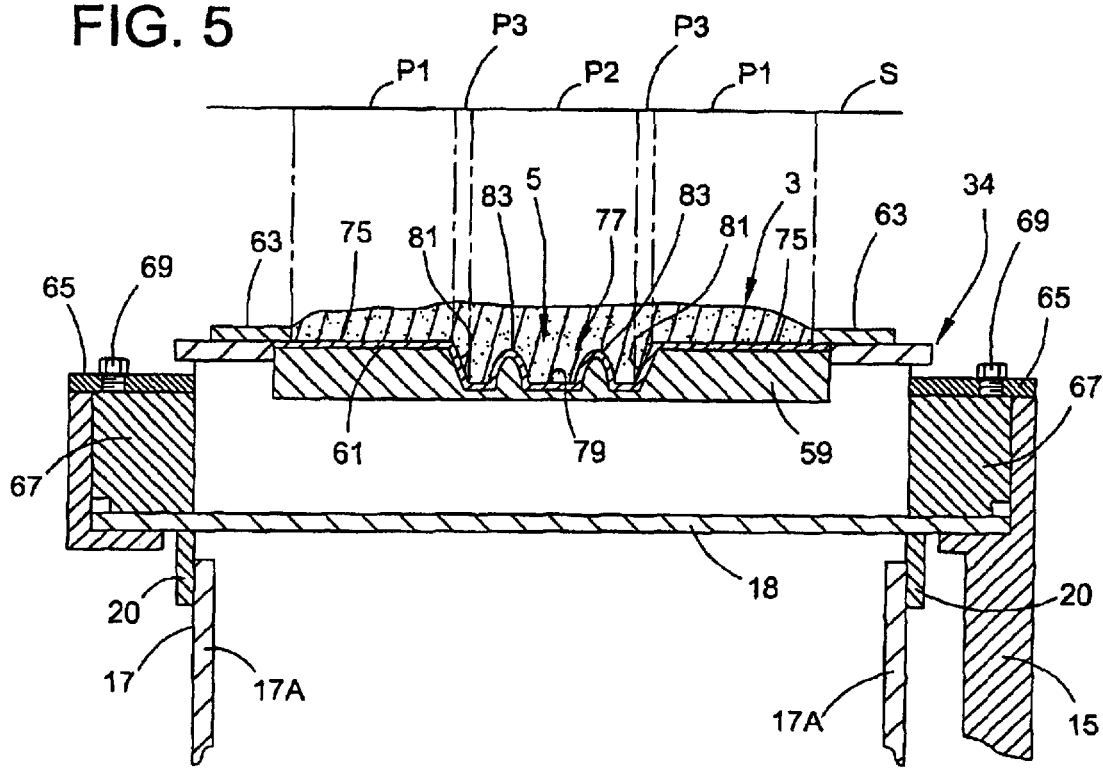
FIG. 5 is a fragmentary section taken in the plane including line 5—5 of FIG. 1A.

Referring now to FIGS. 4 and 5 a single form member 34 from the drum 7 is shown. The forming surface 5 has a length in the machine direction MD and a width in the cross direction CD and is shaped to include a first section 75 at a first depth below the top surface of the masking plate 63. The first section 75 is relatively shallow and planar in configuration for forming a thinner layer of fibrous material. The first section 75 is curved between the ends of the form member 34 in correspondence with the curvature of the drum 7. Thus rather than being truly planar, the first section 75 lies in a smooth surface and is substantially linear in cross section, as may be seen in FIG. 5. It will be noted that the cross section is transverse to the extent of the form member 34 in the machine direction MD. However, the first section 75 may be irregular or have different depths over its area without departing from the scope of the present invention. In that event the "first depth" would be an average depth of the first section 75.

A pocket, indicated generally at 77, includes a bottom surface 79 ("second section") and a transition surface 81 ("third section") connecting the first section 75 with the bottom surface. The terms "top" and "bottom" are used as convenient descriptors given the orientations illustrated in the drawings. However, these terms do not require any absolute orientation of the subject described. The first section 75 can include portions lying on both sides of the bottom surface 79, and in the illustrated embodiment the first section substantially surrounds the pocket 77. The bottom surface 79 (as shown in FIGS. 4 and 5) has a generally undulating configuration which is everywhere below the surface containing the first section 75, and is non-linear in cross section. More particularly, the bottom surface 79 has multiple ridges 83 extending in the machine direction MD the length of the pocket 77. As a result of the ridges 83, the (second) depth of the bottom surface 79 below the first section 75 varies over the area of the bottom surface.

The ridges 83 located within the pocket 77 greatly increase the surface area within the pocket, reducing resistance to air flow (as compared to the first section 75) and thereby promoting the deposit of more fibrous material. Stated another way with reference being made to FIG. 5, the actual surface area of the bottom surface (or "second section") 79 is greater than an area P2 of the bottom surface (or second section) 79 projected onto a generally planar surface S lying directly above the forming surface 5. Although the surface S is generally planar, in fact it has a curvature corresponding to the curvature of the forming surface 5 along its length. The surface area of the bottom surface 79 is measure along its undulating extent over the ridges 83 and so is clearly larger than the projected area P2. FIG. 5 also illustrates the projected area P1 of the first section 75 and the projected area P3 of the transition surface (third section) 81 onto the surface S. The projected areas P1 and P3 are shown to more particularly delineate the projected area P2. In one embodiment, the actual surface area of the bottom surface 79 is at least about 10% larger than the projected surface area P2.

As a result of the surface area of the bottom surface 79, the depth of fibrous material deposited in the pocket 77 is significantly greater than in the first section 75. When the fibrous web 3 is scarfed and cut to define absorbent cores like the absorbent core 38 illustrated in FIG. 6, a liquid holding formation 38A of the absorbent core has its full specified thickness and an upper surface 84 which is substantially flat. In other words, there is no dip in the upper surface 84 of the scarfed absorbent core 38 in the area of the liquid holding formation 38A caused by inadequate deposition of fibrous material in the pocket 77 of the forming surface 5. The liquid holding formation 38A has a sufficiently high basis weight and entanglement of the fibers in the formation is enhanced. Thus, the strength of the holding formation is enhanced without sacrificing the structural integrity of the shallower surrounding regions. The screen side of the liquid holding formation 38A (i.e., the side which engages the forming surface 5 when formed) is formed by the ridges 83 to have two channels 40 extending the length of the pocket 77.

Referring to FIGS. 5 and 6, the surface area of the liquid holding formation 38A on the screen side of the absorbent core 38 is augmented by the shape given to it by the ridges 83 of the forming surface 5. FIG. 6 illustrates the projection of various surfaces of the absorbent core 38 onto a planar surface S'. The projected area of the absorbent core 38 which was formed by the bottom surface 79 of the forming surface 5 is indicated at PC2, the projected area of the core which was formed by the first section 75 is indicated at PC1, and the projected area of the core which was formed by the transition surface 81 is indicated at PC3. The projected area PC1 would be about the same as the surface area of the part of the absorbent core 38 which was formed by the first section 75 (in the illustrated embodiment). The projected area PC3 would be less than the surface area of the part of the absorbent core 38 formed by the transitional surface 81. It will be understood that the actual surface area of that part of the absorbent core formed by the bottom surface 79 will be larger than the projected area PC2 because of the additional surface area provided by the channels 40. For example, the surface area of the part of the absorbent core formed by the bottom surface 79 might be 10% larger than the projected area PC2.

Figure 7:
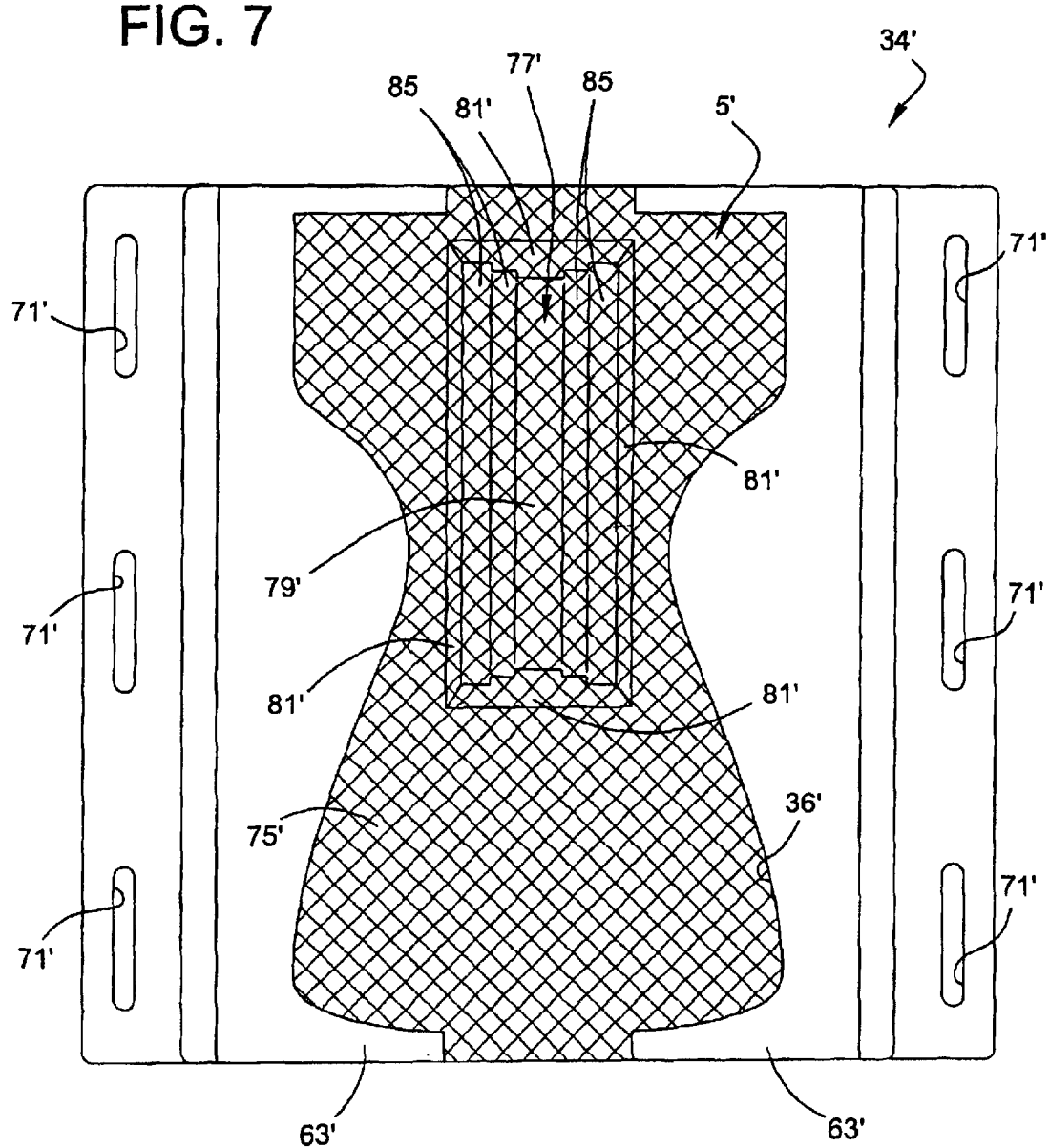
FIG. 7 is a top plan view of a second, modified form member.

A second, modified version of the forming surface 5' is shown in FIGS. 7 and 8. Corresponding parts of the second, modified version of the forming surface 5' will be indicated by the same reference numerals as for the first version of the forming surface 5, followed by a prime. The forming surface 5' includes a first section 75' substantially the same as the first section 75 of the forming surface 5 of FIGS. 4 and 5. A transition surface 81' connects the first section 75' to the bottom surface 79'. However instead of ridges 83, the bottom surface 79' includes two steps 85 extending in the machine-direction MD of the pocket 77'. The provision of the stepped bottom surface 79' within the pocket 77' increases the surface area of the pocket so that more fibrous material will be deposited in the pocket before the region of the perforated plate 61 within the pocket becomes clogged with fibrous material.

A third, modified version of the forming surface 5" is shown in FIG. 9. Corresponding parts of the third, modified version of the forming surface 5" will be indicated by the same reference numerals as for the first version of the forming surface 5, followed by a double prime. The forming surface 5" includes a first section 75" substantially the same as the first section of the forming surface 5 of FIGS. 4 and 5. However instead of ridges 83 or steps 85, the bottom surface 79" is domed in shape and is a smooth curve in transverse cross section. The provision of the dome shape within the pocket 77" increases the surface area of the pocket. In the third, modified version of the forming surface 5", the transition surface 81" is located at the boundary between the first section 75" and the bottom surface 79", but lies in the same smooth surface as the bottom surface.

It will be readily apparent that various conventional devices and techniques can be employed to further process the web 3. For example, the web can be debulked at a debulking station. In addition, various conventional devices and techniques can be employed to sever fibrous web 3 into predetermined lengths to provide selected air formed fibrous articles. The severing system may, for example, include a die cutter, a water cutter, rotary knives, reciprocating knives, energy beam cutters, particle beam cutters or the like, as well as combinations thereof. After severing, the discrete fibrous pads can be transported and delivered for further processing operations, as desired.

Figure 10:
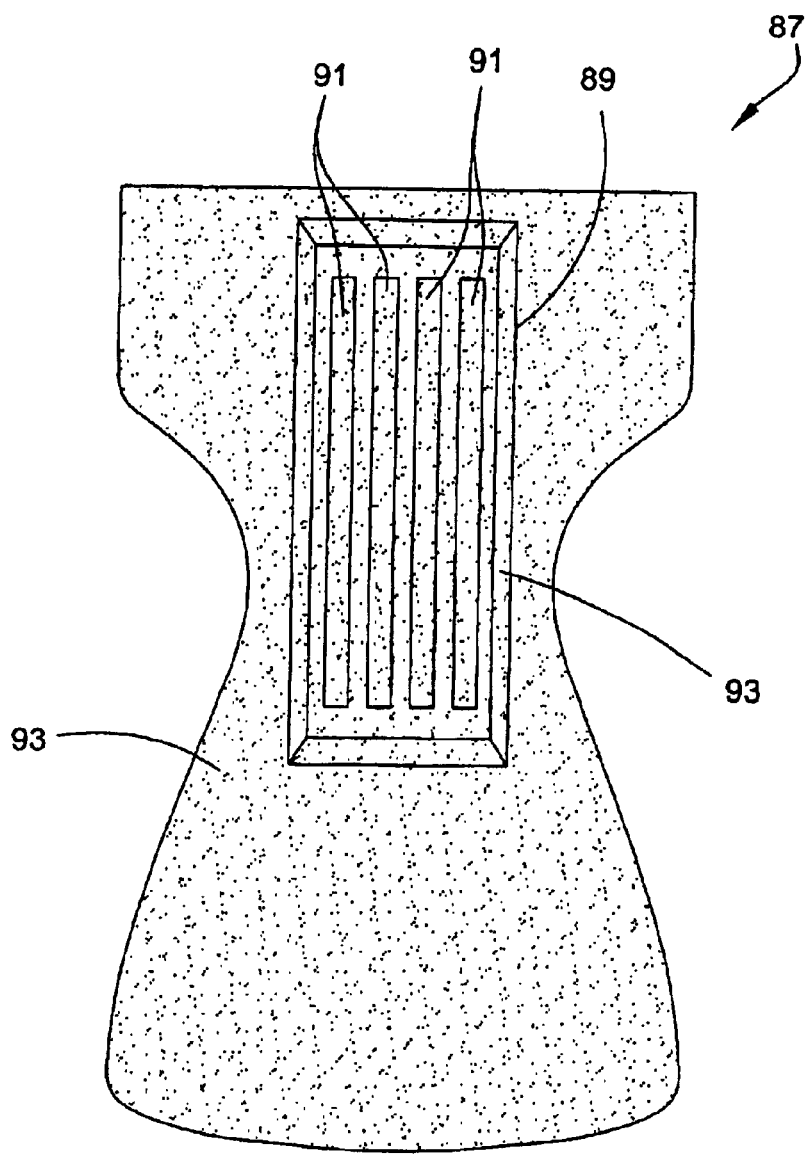
FIG. 10 is another absorbent core.

Referring now to FIG. 10, an absorbent core 87 manufactured using a form having a forming surface (not shown) of the same general type as the forming surface 5 is shown with its screen side facing up so that its liquid holding formation 89 projects out of the page. The absorbent core 87 is shown in the orientation it would occupy leaving the forming drum (e.g., drum 7), which is inverted from the position in which the core is formed at the top of the drum. The forming surface used to make the absorbent core 87 has shapes in its pocket so that the screen side of liquid holding formation 89 of the absorbent core 87 is formed with plural channels 91 extending generally longitudinally of the liquid holding formation. As used herein "generally longitudinally" does not exclude some lateral extension of the channels (not shown). It is to be understood that a liquid holding formation may constitute an entire absorbent core, but as illustrated, the liquid holding formation 89 is surrounded by a thinner outer region 93 also forming part of the absorbent core 87. The channels 91 facilitate distribution of fluid in the liquid holding formation 89. Notably, the channels 91 terminate prior to reaching a peripheral edge 93 of the liquid holding formation 89 which surrounds the channels. This construction helps prevent the fluids from running in the channels 91 completely off of the liquid holding formation 89 before they are absorbed. The channels 91 are formed by ridges on the bottom surface of the forming surface which are closely similar to the ridges 83 shown in FIGS. 4 and 5 which formed the channels 40 of the liquid holding formation 38A. However, the ridges stop short of a transition surface (similar to transition surface 81) in the pocket, thereby spacing the ends of the channels 91 from the edge of the liquid holding formation 89.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. For example, features described in relation to one embodiment may be incorporated into any other embodiment of the invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A form for use in making an air formed fibrous web, the form comprising a foraminous surface having a width and a length greater than said width and adapted to collect fluent fibrous material driven by fluid pressure toward the foraminous surface to form the fibrous web, the foraminous surface including, in cross-section taken across the width of the form, a first section for collecting fluent fibrous material to a first depth, a second section for collecting fluent fibrous material to a second depth greater than the first depth, and a third section connecting the first and second sections, the second section including a bottom surface defining said second depth and having a first portion and a second portion, said second depth being greater at said first portion of the bottom surface than at said second portion, said second portion being in spaced relationship with said third section.

2. A form as set forth in claim 1 wherein the bottom surface of the second section is everywhere spaced below the first section.

3. A form as set forth in claim 1 wherein the first section lies in a generally smooth surface which is substantially linear in cross-section taken across the width of the form.

4. A form as set forth in claim 1 wherein the bottom surface of the second section is undulating in cross-section across the width.

5. A form as set forth in claim 1 wherein the first section has portions on opposite sides of the second section.

6. A form as set forth in claim 1 in combination with other forms of the same construction arranged in a cylinder on a rotatable drum.

7. A form as set forth in claim 1 wherein the surface area of the bottom surface is at least about 10% greater than a projected surface area of the bottom surface.

8. The form set forth in claim 1 in combination with apparatus for forming a fibrous web, said apparatus comprising a delivery chute adapted to deliver fluent fibrous material generally to the form, and a vacuum source for applying a vacuum to draw the fluent material onto the form.

9. The combination as set forth in claim 8 wherein the apparatus further comprises a conveyor for receiving the fibrous web from the form to convey the fibrous web away from the form.

10. The combination as set forth in claim 8 wherein the apparatus further comprises a vacuum device for removing the fibrous web from the form.

11. The combination as set forth in claim 8 wherein the apparatus further comprises a delivery device positioned to deliver a porous substrate to overlie the foraminous surface on the form to receive fibrous material.

12. The combination as set forth in claim 8 wherein the form comprises a series of form members.

13. The combination as set forth in claim 12 wherein the apparatus further comprises a drum mounted for rotation about an axis, the form members being disposed around the circumference of the drum.

14. A form for use in making an air formed fibrous web, the form comprising a foraminous surface having a width and a length greater than said width and adapted to collect fluent fibrous material driven by fluid pressure toward the foraminous surface to form the fibrous web, the foraminous surface including, in cross-section taken across the width of the form, a first section for collecting fluent fibrous material to a first depth and a second section for collecting fluent fibrous material to a second depth greater than the first depth, the second section including a bottom surface defining said second depth and having laterally opposite side edges, said bottom surface having a non-raised portion and at least one raised portion spaced inward of said side edges whereby the second depth of said second section is lesser at said at least one raised portion of the bottom surface than at said non-raised portion.

* * * * *